United States Patent
Kim et al.

(10) Patent No.: US 11,059,852 B2
(45) Date of Patent: Jul. 13, 2021

(54) ERGOSTENOL GLYCOSIDE DERIVATIVE

(71) Applicant: ST PHARM CO., LTD., Siheung-si (KR)

(72) Inventors: Hakwon Kim, Seongnam-si (KR); Tae Hoon Lee, Yongin-si (KR); Hoongyu Park, Suwon-si (KR); Hyunjeong Oh, Seoul (KR)

(73) Assignee: ST PHARM CO., LTD., Siheung-si (KR)

( * ) Notice: Subject to any disclaimer, the term of this patent is extended or adjusted under 35 U.S.C. 154(b) by 0 days.

(21) Appl. No.: 16/518,478

(22) Filed: Jul. 22, 2019

(65) Prior Publication Data

US 2019/0337976 A1 Nov. 7, 2019

Related U.S. Application Data

(63) Continuation-in-part of application No. PCT/KR2017/003183, filed on Mar. 24, 2017.

(30) Foreign Application Priority Data

Jan. 23, 2017 (KR) ........................ 10-2017-0010639

(51) Int. Cl.
| | |
|---|---|
| *C07J 17/00* | (2006.01) |
| *C07H 15/24* | (2006.01) |
| *A61P 17/00* | (2006.01) |
| *A61K 31/7034* | (2006.01) |
| *A61K 8/63* | (2006.01) |

(52) U.S. Cl.
CPC ......... *C07J 17/005* (2013.01); *A61K 31/7034* (2013.01); *A61P 17/00* (2018.01); *C07H 15/24* (2013.01); *A61K 8/63* (2013.01)

(58) Field of Classification Search
None
See application file for complete search history.

(56) References Cited

FOREIGN PATENT DOCUMENTS

| CN | 102940606 A | 2/2013 |
|---|---|---|
| KR | 10-2015-0116410 A | 10/2015 |
| WO | 2015156558 A1 | 10/2015 |

OTHER PUBLICATIONS

Motta et al.—Industrial Crops and Products, 50, 2013, 661-665. (Year: 2013).*
Martin et al., Zeitschrift fuer Naturforschung, C: Journal of Biosciences, 2013, 68(5/6), pp. 253-258. (Year: 2013).*
Laubach et al., "Corticosteroid Intermediates. IV. Synthesis of 11-Oxygenated Steroids from Ergosterol", The Research Laboratoroies of Chas. Pfizer and Co., Inc., 1956, vol. 78, pp. 4746-4756.
Dayal et al., "Rapid hydrogenation of unsaturated sterols and bile alcohols using microwaves", Steroids, 1997, vol. 62, pp. 451-454.
International Search Report for Corresponding International Application No. PCT/KR2017/003183 ( 3 Pages) (dated Oct. 23, 2017).
Tong et al., "Antiviral Activities and Putative Identification of Compounds in Microbial Extracts from the Hawaiian Coastal Waters", Mar. Drugs, 2012, vol. 10, No. 3, pp. 521-538.
Yi et al., "Enhanced oral bioavailability of a sterol-loaded microemulsion formulation of Flammulina velutipes, a potential antitumor drug", International Journal of Nanomedicine, 2012, vol. 7, No. 19, pp. 5067-5078.
Yi et al., "Enhanced Oral Bioavailability and Tissue Distribution of a New Potential Anticancer Agent, Flammulina velutipes Sterols, through Liposomal Encapsulation", Journal of Agricultural and Food Chemistry, 2013, vol. 61, No. 25, pp. 5961-5971.
Misharin et al., "Novel side chain modified Delta 8(14)-15-ketosterols", Steroids, 2007, vol. 72, No. 3, pp. 305-312.
Extended European search report for European patent application No. 17892999.8, dated Aug. 10, 2020, European Patent Office.
Valentina Sepe et al, Marine and Semi-Synthetic Hydroxysteroids as New Scaffolds for Pregnane X Receptor Modulation, Marine Drugs, May 27, 2014, pp. 3091-3115, XP55718392, DOI: 10.3390/md12063091, vol. 12, No. 6.
Mariangela Caroprese et al: A mixture of phytosterols from Dunaliella tertiolecta affects proliferation of peripheral blood mononuclear cells and cytokine production in sheep, Veterinary Immunology and Immunopathology, Nov. 1, 2012, pp. 27-35, XP55718501, Amsterdam, NL ISSN: 0165-2427, DOI: 10.1016/j.vetimm.2012.08.002, vol. 150, No. 1-2.
Isidor Morris Heilbron et al, "CXXI.-Studies in the sterol group. Part III. The acetylation and catalytic hydrogenation of ergosterol",Journal of the Chemical Society, Jan. 1, 1929, pp. 921-926, XP55718848,ISSN: 0368-1769, DOI: 10.1039/JR9290000921.
Frank Stuart Spring, "CCCLIII.-Studies in the sterol group. Part X. The relationship of the fully saturated derivatives of ergosterol and sitosterol", Journal of the Chemical Society, Jan. 1, 1930, pp. 2664-2667, XP55718824, ISSN: 0368-1769, DOI: 10.1039/JR9300002664.

* cited by examiner

*Primary Examiner* — Traviss C McIntosh, III
(74) *Attorney, Agent, or Firm* — Lucas & Mercanti, LLP

(57) ABSTRACT

The present invention provides ergostenol glycoside derivatives, method for preventing, treating, or alleviating dermatitis using the same. The present invention also provides a method for preparing the ergostenol and glycoside derivatives thereof. The ergostenol and the glycoside derivatives thereof according to the present invention suppress the production of chemokines increasing according to the skin inflammation stimulation and inhibit the activity of transcriptional factors controlling the expression of various inflammation mediators in the prevention and treatment of dermatitis.

7 Claims, 3 Drawing Sheets

Specification includes a Sequence Listing.

ERGOSTENOL GLYCOSIDE DERIVATIVE

CROSS-REFERENCE TO RELATED APPLICATIONS

This application is a continuation-in-part of PCT/KR2017/003183 which claims priority from Korean Application No. 10-2017-0010639, filed Jan. 23, 2017, the contents of each of which are incorporated herein by reference.

FIELD OF THE INVENTION

The present invention is related to ergostenol glycoside derivatives and compositions for preventing and treating dermatitis comprising the same.

BACKGROUND OF THE INVENTION

Atopy is traced back to an origin of Greek "a-topos" which has meanings such as "unusual," "strange," "abnormal reaction," etc. Literally, atopy occurs due to complicated entanglement of various causes and repeats its palliation and recurrence.

Atopic diseases include, but not limited to, allergic asthma, allergic conjunctivitis, allergic rhinitis, atopic dermatitis, etc., wherein such diseases may occur alone or in combination simultaneously.

An exact cause of the currently known atopic diseases has not been found yet. However, experts generally believe that genetic and immunological factors are involved in such occurrence, while other environmental and mental factors, etc., may also serve to aggravate the diseases.

Atopic dermatitis is one of the most common skin diseases in infants and young children, starting at the rate of 45% for the first six months after birth, 60% before the first 12 months after birth, and at least 85% before five years old. Generally, atopic dermatitis is known as a transient disease in childhood, and in about 50% of patients with such disease the symptoms would disappear before the second birthday. However, 25% thereof continue to suffer from such symptoms until the adolescent period, while the remaining 25% thereof continues to have such symptoms through the adulthood.

A main symptom of atopic dermatitis is itchiness. Further, a series of vicious cycles are repeated, in such a way that scratching and itching the spot may cause eczematous lesions, thus growing into more serious pruritus.

The pharmaceutical compositions currently used for treating skin immune diseases contain steroids, anti-histaminic agents, immunomodulators, etc., among which steroidal drugs are known to have the most excellent effect of anti-inflammation and immunosuppression. However, long term use of these compositions such as steroids are known to cause side effects, such as hair growth on the applied skin area; skin atrophy; a decrease in the pigments of skin; skin thinning; and the like.

For example, one of the most widely used therapeutic agents for atopic dermatitis is dexamethasone, which is known as a steroid. However, dexamethasone is effective only in short-term treatment, but the stability and efficacy thereof have not been established yet in long-term treatment for one year or more, and even cases of side effects such as skin thinning, atrophy, scars, discoloration, etc. have been reported.

Alternatively, corticosteroid is known to inhibit IgE, which is an inflammation-mediating cytokine, and thus palliate atopy (Peter J. Barnes, Corticosteroids, IgE, and atopy., J Clin Invest. 2001 Feb 1; 107(3): 265-266). However, corticosteroid is somewhat unsuitable to be used as a standard therapeutic agent due to the side effects of a steroid material. Also, pimecrolimus and tacrolimus have recently drawn much attention as an immunomodulator for treating atopy (Cury Martins J et al, Topical tacrolimus for atopic dermatitis., Cochrane Database Syst Rev. 2015 Jul. 1). However, pimecrolimus and tacrolimus have a problem of lowering immunity and thus becoming susceptible to infections with other diseases.

Accordingly, there is a need for an alternative composition and treatment for effectively preventing or treating atopic dermatitis soaring, while minimizing the side effects of chemical drugs.

SUMMARY OF THE INVENTION

The present invention provides novel ergostenol glycoside derivatives for preventing, treating and alleviating dermatitis such as atopy, etc.

Alternatively, the present invention provides ergostenol glycoside derivatives, represented by Formula 1, or pharmaceutically acceptable salts thereof:

[Formula 1]

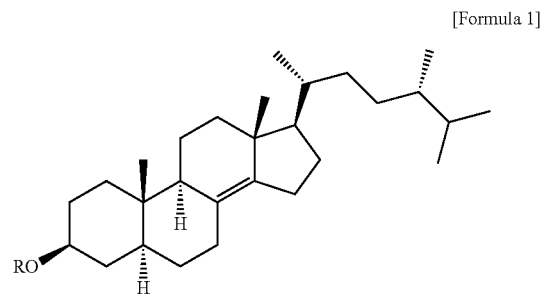

wherein R is a monosaccharide or an amino sugar,
wherein the monosaccharide has at least two hydroxy groups and a carbonyl group adjacent thereto, and is a monomer of carbohydrate, which is represented by a general formula of $C_n(H_2O)_n$; and
wherein the amino sugar is a monosaccharide, wherein one or more of the hydroxy groups (OH) of the monosaccharide is replaced with an amino group.

DETAILED DESCRIPTION OF THE INVENTION

A certain embodiment of the present invention provides novel ergostenol glycoside derivatives, or alternatively, pharmaceutical compositions for preventing or treating dermatitis, containing ergostenol or a glycoside derivative thereof, or methods for preventing or treating dermatitis, comprising administering a composition containing ergostenol or a glycoside derivatives thereof into subjects in need.

Another embodiment of the present invention provides cosmetic compositions for alleviating or palliating dermatitis, containing ergostenol or a glycoside derivatives thereof.

Alternate embodiment of the present invention provides methods for preparing ergostenol or glycoside derivatives thereof, or alternatively, methods for preparing a pharmaceutical composition for preventing or treating dermatitis using ergostenol or a glycoside derivatives thereof.

The ergostenol and a glycoside derivatives thereof of the present invention have remarkable efficacies of alleviating and treating the symptoms of dermatitis and atopic dermatitis, and have also developed a method for preparing the ergostenol and the glycoside derivative thereof for the first time with ergosterol as a starting material, thereby completing the present invention.

An embodiment of the present invention provides novel ergostenol glycoside derivatives, represented by Formula 1, or pharmaceutically acceptable salts thereof:

[Formula 1]

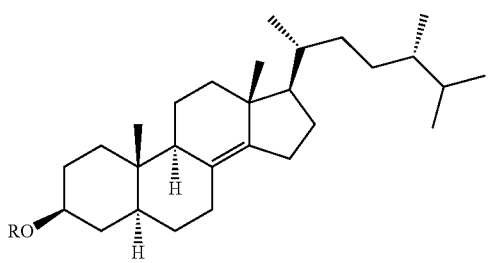

wherein R is a monosaccharide or an amino sugar, wherein,
the monosaccharide has at least two hydroxy groups and a carbonyl group adjacent thereto, and is a monomer of carbohydrate, which is represented by a general formula of $C_n(H_2O)_n$, preferably a hexose or a pentose; and
the amino sugar is a compound, in which a part (for example, one hydroxy group) of hydroxy groups (OH) in the monosaccharide is replaced with an amino group.

Particularly, the amino sugar is glucosamine or galactosamine.

The monosaccharide of Formula 1 can be a hexose selected among glucose, galactose, xylose and mannose represented by formulas of

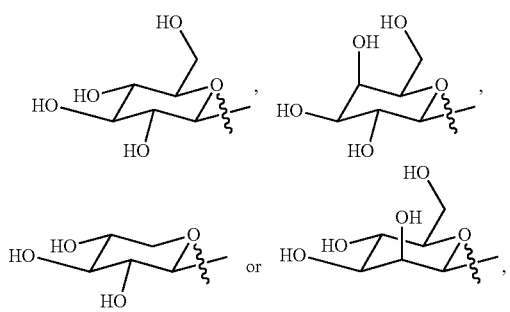

respectively.

The monosaccharide of Formula 1 can be a pentose represented by a formula of

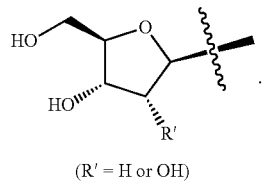

(R' = H or OH)

The amino sugar of Formula 1 is a monosaccharide wherein one of the hydroxyl group (OH) is replaced with an amino group. Particularly, the amino sugar is glucosamine or galactosamine. For example, an amino group of amino sugar is an acetylated one. Particularly, such group is N-acetylglucosamine represented by a formula of

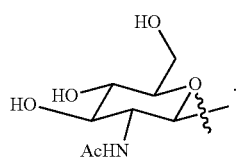

Figure 1:
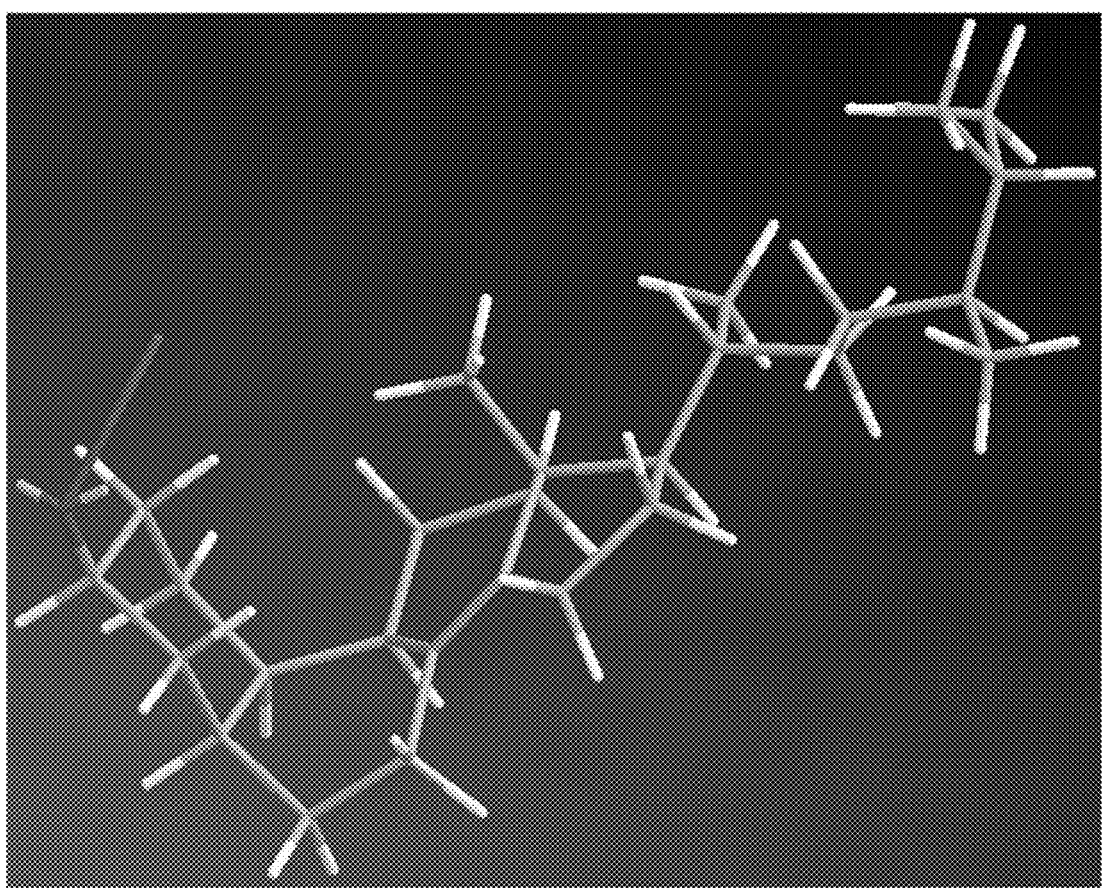
FIG. 1 presents three-dimensional stereostructure of an ergostenol glycoside derivative of the present invention.

The ergostenol of the present invention has a double bond between carbon-8 and carbon-14, thus having a unique steric conformation, unlike general steroid compounds. Particularly, the ergostenol and the glycoside derivative thereof may have a three-dimensional stereostructure as presented in FIG. 1.

The Pharmaceutically Acceptable Salts

The pharmaceutically acceptable salts in the present invention can be an inorganic ion salts prepared from calcium, potassium, sodium, magnesium and the like; an inorganic acid salts prepared from hydrochloric acid, nitric acid, phosphoric acid, bromic acid, iodic acid, perchloric acid, tartaric acid, sulfuric acid and the like; an organic acid salts prepared from acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbric acid, carbonic acid, vanillic acid, hydroiodic acid, mandelic acid, mucic acid, nitric acid, pamoic acid, panthothenic acid, succinic acid, tartaric acid, etc.; a sulfonic acid salts prepared from methanesulfonic acid, ethanesulfonic acid, benzenesulfonic acid, p-toluenesulfonic acid, camphorsulfonic acid, naphthalenesulfonic acid or the like; an amino acid salts prepared from glycine, arginine, lysine, etc.; an amine salts prepared from trimethylamine, triethylamine, ammonia, pyridine, picoline, etc.; or a mixture thereof, the like, but not limited to those listed.

For example, the pharmaceutically acceptable salts is hydrochloric acid as an inorganic acid and methanesulfonic acid as an organic acid.

Pharmaceutical Compositions For Preventing Or Treating Dermatitis

The present invention also provides pharmaceutical compositions for preventing or treating dermatitis, containing ergostenol, glycoside derivatives thereof represented by Formula 1 or pharmaceutically acceptable salts thereof.

The dermatitis includes atopic dermatitis, contact dermatitis or seborrheic dermatitis, and particularly atopic dermatitis.

Figure 2:
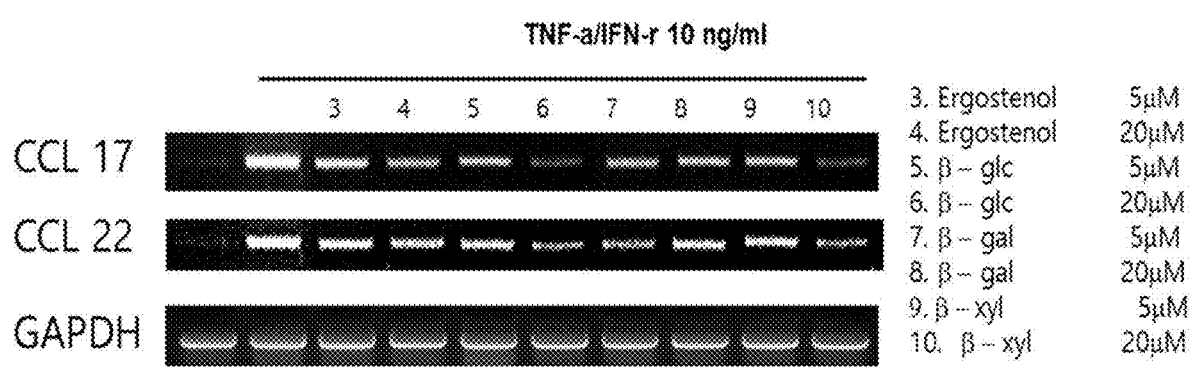
FIG. 2 presents results, in which ergostenol and a glycoside derivative thereof inhibit the CCL17 and CCL22 gene expressions in keratinocyte cell lines, i.e., HaCaT cells according to the induction of TNF-α and IFN-γ.
Figure 3:
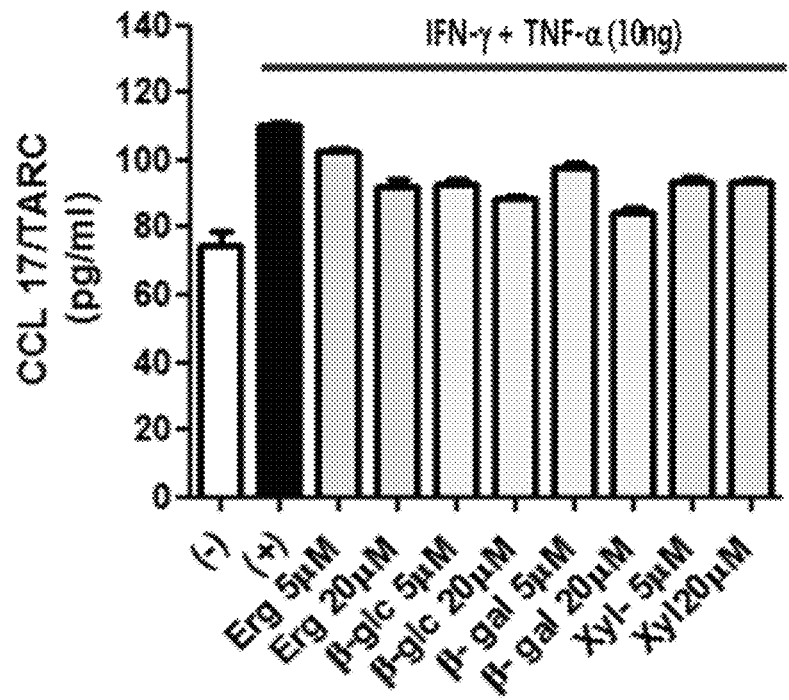
FIG. 3 presents graph of identifying results, in which an ergostenol derivative inhibits the CCL17 and CCL22 protein expressions in keratinocyte cell lines, i.e., HaCaT cells according to the induction of TNF-α and IFN-γ.
Figure 3:
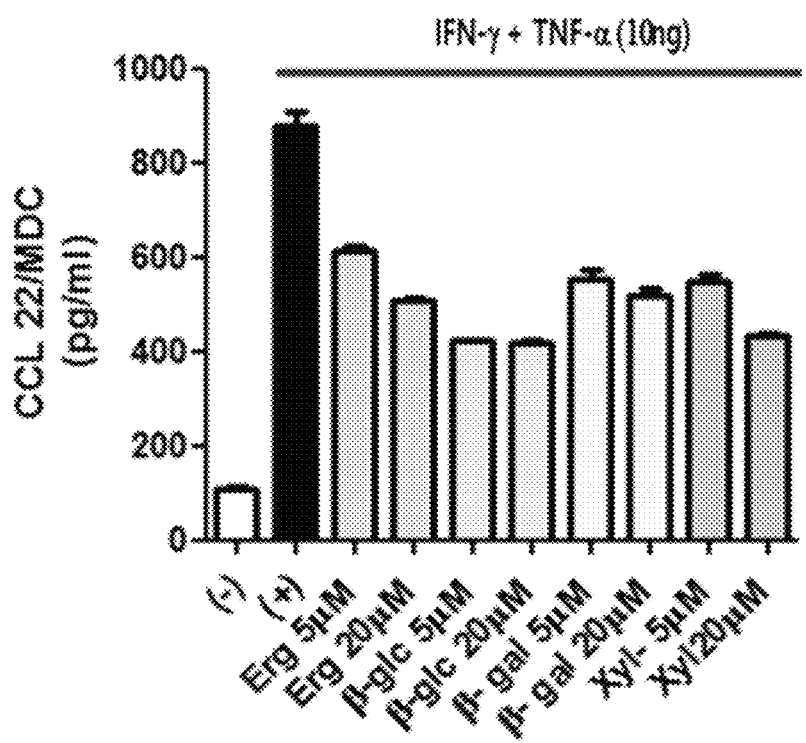

In one specific exemplary embodiment of the present invention, it was identified that there is a decrease in a level of CCL17 and CCL22 gene and protein expressions in a concentration-dependent way, when HaCaT cells are treated with the ergostenol and the glycoside derivative thereof (FIGS. 2 and 3). Thus, without bound to a theory, the ergostenol and the glycoside derivatives thereof of the present invention control an inflammation-mediating expression of keratinocyte cell lines, thus exhibiting an activity of palliating dermatitis.

In the present invention, a pharmaceutical composition is a dosage form selected from the group consisting of ointments, gels, creams, patches and aerosols. Also, the pharmaceutical composition is an oral preparation or an injectable preparation. The oral preparation is powders, granules, tablets, capsules, liquid suspensions, emulsions, syrups, aerosols, suspensions, liquids for internal use, oily agents or syrup preparations, and the injectable preparation is a dosage form in a sterilized injection form.

The pharmaceutical composition of the present invention is formulated into preparations with the addition of pharmaceutically acceptable carriers, wherein the content on such formulation is understood with reference to Remington's Pharmaceutical Science (latest version), Mack Publishing Company, Easton Pa. The pharmaceutically acceptable carriers mean the ones conventionally used by those skilled in the field of medicinal invention for preparing pharmaceutical compositions. For example, there are lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil and the like. Also, the pharmaceutically acceptable carriers include diluents or excipients such as fillers, bulking agents, binders, humectants, disintegrants, surfactants, etc. For example, an oral solid preparation may include tablets, pills, powders, granules, capsules, etc., which may contain at least one excipient, for example, starch, calcium carbonate, sucrose, lactose, gelatin or the like, and may contain lubricants, etc., such as magnesium stearate and talc. An oral liquid preparation may include suspensions, liquids for internal use, oily agents, syrup preparations, etc., and may also contain diluents, humectants, sweetening agents, flavoring agents, preservatives, etc. such as water, liquid paraffin, etc. A parenteral preparation includes sterilized aqueous solutions, nonaqueous solvents, suspensions, oily agents, freeze-dried preparations. The nonaqueous solvents and suspensions include propylene glycol; polyethylene glycol; vegetable oils such as olive oil; injectable esters such as ethyl oleate; etc. However, the present invention is not limited to the pharmaceutically acceptable carriers listed above, etc., and such carriers are provided as illustrations only. The carriers may include non-naturally occurring carriers.

A dosage of the pharmaceutical composition varies depending on a patient's condition and weight, a degree of disease, a drug form, an administration route and period, but is appropriately selected as circumstances require. For example, the ergostenol or the glycoside derivative thereof is administered or applied onto skin, etc. in an amount of 0.01 mg/kg to 10 mg/kg per a day and preferably 2.5 mg/kg to 5 mg/kg per a day. Such administration or application is performed once a day, or divided into several times a day. Also, the pharmaceutical composition may contain the ergostenol or the glycoside derivative thereof in an amount of 0.0001 to 80 wt % with regard to the total weight of the composition. The pharmaceutical composition is administered into mammals such as humans via various routes, for example, by means of oral, intravenous, intramuscular or subcutaneous injection.

Also, the pharmaceutical composition of the present invention may further contain at least one active ingredient capable of alleviating, palliating, treating or preventing dermatitis in addition to the ergostenol or the glycoside derivative thereof.

Further, the pharmaceutical composition of the present invention is used alone or in combination with surgery, endocrinotherapy, drug treatment and methods of using a biological response modifier, in order to alleviate, palliate, treat or prevent dermatitis.

Cosmetic Compositions For Alleviating Or Palliating Dermatitis

The present invention also provides cosmetic compositions for alleviating or palliating dermatitis, containing ergostenol or a glycoside derivatives thereof. The dermatitis is the same as described above.

In the present invention, the cosmetic composition is a dosage form selected from the group consisting of skin lotion, astringent lotion, nourishing lotion, nourishing cream, massage cream, essence, eye cream, eye essence, cleansing cream, cleansing foam, cleansing water, pack, powder, body lotion, body cream, body oil, body essence, makeup base, foundation, hairdye, shampoo, conditioner and body cleanser.

The cosmetic composition of the present invention is prepared into various forms according to a conventional method for preparing cosmetics by using the ergostenol or the glycoside derivative thereof, and may contain conventional adjuvants such as stabilizers, solubilizers, vitamins, pigments and flavoring agents, which are conventionally used in a cosmetic composition field.

Also, if the cosmetic composition is prepared into a form of cosmetic product, shampoo, hair lotion, hair cream, hair gel, etc. containing the ergostenol or the glycoside derivative thereof, such composition is used by being diluted with conventional cleansing liquid, astringent liquid and moisturizing liquid.

The cosmetic composition of the present invention may contain the ergostenol or the glycoside derivative thereof in an amount of 0.001 to 20 wt % based on the total weight of the composition.

Methods For Preventing Or Treating Dermatitis

The present invention provides a method for preventing or treating dermatitis, comprising a step of administering a therapeutically effective amount of ergostenol or a glycoside derivative thereof into subjects in need.

As used herein, the term "therapeutically effective amount" refers to an amount of the ergostenol or the glycoside derivative thereof, which is effective in preventing or treating dermatitis.

The method for preventing or treating dermatitis according to the present invention, in particular, the method for preventing or treating atopic dermatitis includes not only dealing with the disease itself before the expression of its symptoms but also inhibiting or avoiding such symptoms by administering (applying onto skin) the ergostenol or the glycoside derivative thereof. In managing the disease, a preventive or therapeutic dose of a certain active ingredient may vary depending on a nature and severity of the disease or condition and a route of administering the active ingredient. Such ergostenol or the glycoside derivative thereof is preferably administered or applied onto skin, etc., in an amount of 0.01 mg/kg to 10 mg/kg per a day, and more preferably 2.5 mg/kg to 5 mg/kg per a day, and the administration or application is performed once a day or divided into several times a day. However, a dose and a frequency thereof may vary depending on an individual patient's age, weight and reaction, and a suitable dose and usage is easily selected by those having ordinary skill in the art, naturally considering such factors.

Also, the method for preventing or treating dermatitis according to the present invention may further include administering a therapeutically effective amount of an additional active agent, which is helpful in treating the disease, along with the ergostenol or the glycoside derivative thereof, and the additional active agent may exhibit a synergy effect or an additive effect together with the ergostenol or the glycoside derivative thereof.

Preparation of Pharmaceutical Compositions For Preventing Or Treating Dermatitis The ergostenol or glycoside derivatives thereof can be used in preparing a pharmaceutical composition for preventing or treating dermatitis, in particular, atopic dermatitis. The ergostenol or the glycoside derivative thereof for preparing a drug is combined with acceptable adjuvants, diluents, carriers, etc., and is prepared into a complex preparation together with other active agents, thus having a synergy action of active components.

Matters mentioned in the use, composition and treating method of the present invention are equally applied, if not contradictory to each other.

Methods for Preparing Ergostenol and The Glycoside Derivatives Thereof

Also, another aspect provides an efficient method for preparing the ergostenol and the glycoside derivative thereof comprising:
hydrogenating ergosterol to prepare ergostenol;
reacting ergostenol with a sugar having protecting group on OH groups to obtain protected form of an ergostenol glycoside; and
deprotecting the protecting groups on OH of the sugar to obtain an ergostenol glycoside.

First, ergostenol is prepared from ergosterol, which is commonly present in the natural world, as a starting material. Particularly, the method includes a step of reacting ergosterol with a Pd/C catalyst in the presence of an alcohol solvent and a chlorinated organic solvent to obtain ergostenol. Other hydrogenating method known in the art can also be used to reduce one of the two double bonds in ergosterol.

The chlorinated organic solvent is selected, but not limited, from the group consisting of methylene chloride, chloroform and 1,2-dichloroethane, and the alcohol solvent is methanol, ethanol or propanol.

In the step, hydrogen is filled thereinto, then stirred at room temperature for long hours, then filtered with Celite, and then concentrated under reduced pressure. A concentrated solid is subjected to recrystallization by means of methanol and filtered to obtain ergostenol.

The glycoside derivative of ergostenol is prepared by including a step of mixing the ergostenol with a sugar having protected OH group(s) and/or amine (NH) group(s) in the presence of a chlorinated organic solvent.

The OH group of the sugar is protected with a benzoyl groups or other proper protecting groups such as acetyl, trifluoroacetyl (TFA), trimethylacetyl (Piv), 4-acetoxy-2,2-dimethylbutanoyl, tert-butoxycarbonyl (t-BOC), tert-butyldimethylsilyl (TBDMS), trimethylsilyl (TMS), triisopropyldisilyl (TIPDS), methylsulfonylethoxycarbonyl, p-toluyl, 2,2,2-trichloroethoxycarbonyl (Troc), triphenylmethyl (trityl or Tr), tetrahydropyranyl (THP), acetonide, benzylidene, cyclohexane-1,2-diacetal, or a mixture thereof.

The OH group, in which a glucosylation reaction is to take place, may take a form in which such group is pyranosylated and bound to trichloroacetimidate.

The chlorinated organic solvent is selected from the group consisting of methylene chloride, chloroform and 1,2-dichloroethane.

The amino groups of the sugar are protected for the reaction with ergostenol, i.e. glycosylation, with a proper protecting groups such as but not limited to, tert-butoxycarbonyl (t-BOC), N-tetrachlorophthaloyl (TCP), carboxybenzyl (Cbz), or acetyl.

The acid catalyst is selected from the group consisting of TMSOTf, $BF_3OEt_2$, $Cu(OTf)_2$, $Sc(OTf)_3$, $SiO_2$—$H_2SO_4$ and cellulose-$HClO_4$. In this step, stirring is performed at room temperature, after which organic base (for example, TEA) is added into a reacting solution, neutralized, filtrated, and then concentrated under reduced pressure.

From the step, an ergostenol glycoside derivative with sugar having the protected OH and/or NH group is obtained, and the ergostenol glycoside derivative of the present invention is finally obtained through deprotection.

The hydroxy or amine protecting groups in the glycosylated ergostenol are removed or deprotected by stirring the ergostenol glycoside in the presence of an acid or base catalyst or any other proper method specific for each protecting group known in the art.

Particularly, the ergostenol glycoside derivative is obtained by adding NaOMe or $K_2CO_3$ to the ergostenol glycoside derivative having the benzoyl protected OH groups in the presence of the chlorinated organic solvent and the alcohol solvent and stirring a resulting mixture at room temperature.

Advantageous Effects

Ergostenol and a glycoside derivative thereof according to the present invention suppress the production of chemokines increasing according to the skin inflammation stimulation and inhibit the activity of transcriptional factors controlling the expression of various inflammation mediators in the prevention and treatment of dermatitis, and thus is favorably used as an agent for preventing and treating dermatitis or as a cosmetic material for alleviating atopy.

EXAMPLES

Hereinafter, the present invention will be described in more detail through the following examples. However, the following examples are provided only for the purpose of illustrating the present invention, and thus the scope of the present invention is not limited thereto.

Preparation Example 1

Preparation for Ergostenol

Ergosterol (3 g) was dissolved in methylene chloride (30 mL) and methanol (70 mL), after which palladium carbon (0.3 g) was added thereinto. Hydrogen was filled thereinto and stirred at room temperature for 20 hours. After that, a resulting mixture was filtered via Celite and immediately concentrated under reduced pressure. A concentrated solid was subjected to recrystallization by means of methanol and filtered to obtain a white solid product at a yield rate of 99% (3 g).

$^1$H NMR (300 MHz, CDCl$_3$) δ (ppm): 3.62 (brs, 1H), 2.39-2.35 (m, 1H), 2.20-2.17 (m, 2H), 1.95-1.91 (m, 1H), 1.83-1.80 (m, 2H), 1.17-1.54 (m, 7H), 1.45-1.30 (m, 7H), 1.27-1.25 (m, 5H), 1.10-1.06 (m, 5H), 1.01-0.97 (m, 1H), 0.97-0.91 (m, 3H) 0.85 (d, 6H, J=7.9 Hz), 0.78 (d, 6H, J=6.6 Hz), 0.69 (s, 3H)

$^{13}$C NMR (75 MHz, CDCl$_3$) δ (ppm): 142.7, 126.3, 71.3, 56.7, 49.3, 44.3, 42.7, 39.1, 38.3, 37.3, 36.8, 36.5, 34.8, 33.5, 31.6, 31.5, 30.4, 29.6, 28.9, 27.0, 25.8, 20.5, 20.0, 19.3, 18.2, 17.6, 15.4, 12.8

Preparation Example 2

Preparation for Ergostenol-Glucose

2-1. Preparation for 2,3,4,6-tetrabenzoyl Glucose-Ergostenol

Ergostenol (0.1 g) and 2,3,4,6-tetra-O-benzoyl-a-D-glucopyranosyl trichloroacetimidate (0.37 g) were dissolved in methylene chloride (2.5 mL), after which 4 A molecular sieves were inserted thereinto and stirred at room temperature. TMSOTf (4.5 μL) was added thereinto and stirred at room temperature for 2.5 hours. TEA (1 mL) was added into the reacting solution, neutralized, and then filtrated, such that a resulting filtrate was concentrated under reduced pressure. A resulting concentrate was purified via column chromatography to obtain a product at a yield rate of 90%.

2-2. Preparation for Ergostenol-Glucose 2,3,4,6-tetrabenzoyl glucose-ergostenol (0.46 g) obtained in the Preparation Example 2-1 was dissolved in methylene chloride (5 mL) and methanol (5 mL), after which 0.5 M NaOMe (5.6 mL) was added thereinto and stirred at room temperature for 1.5 hours. Dowex Mac-3 was inserted thereinto, neutralized, and then filtrated, such that a resulting filtrate was concentrated under reduced pressure. A resulting concentrate was purified via column chromatography to obtain a product at a yield rate of 71%.

$^1$H NMR (300 MHz, Pyridine-d$^5$) δ (ppm): 5.11 (d, 1H, J=7.7 Hz), 4.65-4.68 (m, 1H), 4.44-4.50 (m, 1H), 4.28-4.39 (m, 2H), 4.03-4.12 (m, 3H), 2.36 (d, 1H, J=14.5 Hz), 2.25-2.28 (m, 2H), 2.06 (m, 1H), 1.83-1.96 (m, 4H), 1.32-1.61 (m, 11H), 1.06-1.21 (m, 8H), 0.99-1.01 (m, 4H), 0.88-0.90 (m, 6H), 0.81-0.85 (m, 6H), 0.63 (s, 3H)

$^{13}$C NMR (75 MHz, Pyridine-d$^5$) δ (ppm): 142.61, 126.85, 102.10, 78.69, 78.62, 76.94, 75.41, 71.84, 62.99, 57.01, 49.56, 44.06, 42.97, 39.37, 37.57, 37.15, 36.75, 35.08, 34.87, 33.81, 31.77, 30.72, 30.09, 29.91, 29.26, 27.37, 26.13, 20.68, 20.23, 19.50, 18.51, 17.77, 15.63, 12.83

Preparation Example 3

Preparation for Ergostenol-Galactose

3-1. Preparation for 2,3,4,6-tetrabenzoyl Galactose-Ergostenol

Ergostenol (0.136 g) and 2,3,4,6-tetra-O-benzoyl-a-D-galactopyranosyl trichloroacetimidate (0.5 g) were dissolved in methylene chloride (10 mL), after which 4 A molecular sieves were inserted thereinto and stirred at room temperature. Cellulose-HClO$_4$ (0.17 mmol/g, 60 mg) was added thereinto and stirred at room temperature for a day. The reacting solution was filtered, after which a resulting filtrate was concentrated under reduced pressure. A resulting concentrate was purified via column chromatography to obtain a product at a yield rate of 79%.

3-2. Preparation for Ergostenol-Galactose 2,3,4,6-tetrabenzoyl galactose-ergostenol (0.39 g) obtained in the Preparation Example 3-1 was dissolved in methylene chloride (4 mL) and methanol (4 mL), after which 0.5 M NaOMe (4.8 mL) was added thereinto and stirred at room temperature for two hours. Dowex Mac-3 was inserted thereinto, neutralized, and then filtered, such that a resulting filtrate was concentrated under reduced pressure. A resulting concentrate was purified via column chromatography to obtain a product at a yield rate of 80%.

$^1$H NMR (300 MHz, Pyridine-d$^5$) δ (ppm): 5.02 (d, 1H, J=7.5 Hz), 4.63 (s, 1H), 4.48-4.54 (m, 3H), 4.20-4.28 (m, 2H), 4.04 (m, 1H), 2.37 (d, 1H, J=14.5 Hz), 2.25 (m, 2H), 2.09 (m, 1H), 1.83-1.93 (m, 4H), 1.34-1.61 (m, 11H), 1.06-1.19 (m, 8H), 0.99-1.01 (m, 4H), 0.88-0.90 (m, 6H), 0.82-0.85 (m, 6H), 0.62 (s, 3H)

$^{13}$C NMR (75 MHz, Pyridine-d$^5$) δ (ppm): 142.60, 126.86, 102.69, 77.11, 76.80, 75.48, 72.76, 70.45, 62.70, 57.01, 49.56, 44.08, 42.97, 39.37, 37.57, 37.14, 36.77, 35.08, 34.89, 33.81, 31.76, 30.72, 30.11, 29.92, 29.27, 27.36, 26.12, 20.67, 20.22, 19.49, 18.50, 17.76, 15.63, 12.81

Preparation Example 4

Preparation for Ergostenol-Xylose

4-1. Preparation for 2,3,4-tribenzoyl Xylose-Ergostenol

Ergostenol (0.5 g) and 2,3,4-tri-O-benzoyl-a-D-xylopyranosyl trichloroacetimidate (1.5 g) were dissolved in methylene chloride (30 mL), after which 4A molecular sieves were inserted thereinto and stirred at room temperature. Cellulose-HClO$_4$ (0.17 mmol/g, 0.22 g) was added thereinto and stirred at room temperature for a day. The reacting solution was filtered, after which a resulting filtrate was concentrated under reduced pressure. A resulting concentrate was purified via column chromatography to obtain a product at a yield rate of 82%.

4-2. Preparation for Ergostenol-Xylose 2,3,4-tribenzoyl xylose-ergostenol (0.86 g) obtained in the Preparation Example 4-1 was dissolved in methylene chloride (10 mL) and methanol (10 mL), after which 0.5 M NaOMe (12 mL) was added thereinto and stirred at room temperature for two hours. Dowex Mac-3 was inserted thereinto, neutralized, and then filtered, such that a resulting filtrate was concentrated under reduced pressure. A resulting concentrate was purified via column chromatography to obtain a product at a yield rate of 70%.

$^1$H NMR (300 MHz, Pyridine-d$^5$) δ (ppm): 4.95 (d, 1H, J=7.5 Hz), 4.42-4.48 (m, 1H), 4.22-4.35 (2H, m), 4.05 (t, 1H, J=8.0 Hz), 3.96 (m, 1H), 3.83 (t, 1H, J=10.3 Hz), 2.37 (d, 1H, J=12.6 Hz), 2.25-2.28 (m, 2H), 2.11 (m, 1H), 1.84-1.97 (m, 4H), 1.36-1.65 (m, 11H), 1.04-1.32 (m, 9H), 1.00 (d, 3H, J=6.4 Hz), 0.88-0.90 (m, 6H), 0.81-0.85 (m, 6H), 0.64 (s, 3H)

$^{13}$C NMR (75 MHz, Pyridine-d$^5$) δ (ppm): 142.65, 126.84, 103.04, 78.59, 77.31, 75.16, 71.28, 67.23, 57.03, 49.57, 44.23, 42.99, 39.38, 37.58, 37.17, 36.85, 35.09, 34.94, 33.81, 31.76, 30.73, 30.22, 29.92, 29.27, 27.38, 26.13, 20.68, 20.25, 19.51, 18.51, 17.77, 15.63, 12.84

Example 1

Identification of an Effect of Ergostenol and a Glycoside Derivative Thereof on Inhibiting an Increase in CCL17 and CCL22 Expressions As HaCaT cells were treated with ergostenol and a glycoside derivative thereof, it was identified that there is an effect of reducing CCL17 and CCL22 expressions induced by TNF-α and/or IFN-γ known as an inflammation-inducing molecule.

1×10$^6$ HaCaT cells were moved into a 6-well microplate, cultured in DMEM containing 10% (v/v) FBS for 12 hours, washed with PBS, and then treated in 2 mL of serum free media with ergostenol at each concentration of 2.5, 5, 10 and 20 μg/mL for one hour. After that, the cells were treated with inflammation-inducing molecules, i.e., TNF-α, IFN-γ, or TNF-α and IFN-γ, and then cultured for 18 hours.

To identify a change in CCL17 and CCL22 expressions at an RNA level, RNAs were isolated with Trizol reagent kit (Invitrogen, Gaithersburg, Md.) according to a manufacturer's manual. A reverse transcription was performed with the isolated RNAs as a template to obtain cDNAs.

A reverse transcription buffer solution (5 mM MgCl$_2$, 1 mM dNTP, 2.5 U/μL reverse transcriptase, and 2.5 μM oligo (dT) 15 as a primer (omniscript RTkit, Qiagen)), 0.5 U of RNase inhibiter, 2.5 μM of oligo (dT) and 2.5 U of reverse transcriptase were added into 2 μg of cDNAs, and subjected to reaction at 37° C., such that the cDNAs were obtained.

To quantify the obtained cDNAs, PCR was performed with the primers of a following table 1, after which the amplified DNAs were identified with 1% agarose gel.

TABLE 1

| Primer | Primer Sequence |
| --- | --- |
| Forward CCL-17 (SEQ ID No. 1) | 5'-ctt ctc tgc agc aca tcc-3' |
| Reverse CCL-17 (SEQ ID No. 2) | 5'-aag acc tct caa ggc ttt g-3' |
| Forward CCL-22 (SEQ ID No. 3) | 5'-agg aca gag cat ggc tcg cct aca ga-3' |
| Reverse CCL-22 (SEQ ID No. 4) | 5'-taa tgg cag gga ggt agg gct cct ga-3' |
| Forward β-actin (SEQ ID No. 5) | 5'-gcg gga aat cgt gcg tga cat t-3' |
| Reverse β-actin (SEQ ID No. 6) | 5'-gat gga gtt gaa ggt agt ttc gtg-3' |

Also, to figure out an effect of ergostenol at a protein level, HaCaT cells were treated with ergostenol at a concentration of 2.5, 5, 10 and 20 μg/mL for one hour, then treated with molecules related to inflammation induction, i.e., TNF-α, IFN-γ, or TNF-α and IFN-γ, and then cultured for 18 hours. With regard to CCL17 and CCL22, the amount of proteins present in media was identified with an ELISA kit (R&D Systems, Minneapolis, Minn., USA). Captured antibodies (anti-CCL17 antibody and anti-CCL22 antibody) at 2 μg/mL were inserted into a 96-well plate in an amount of 50 μL, respectively, subjected to coating for two hours, and then subjected to blocking with PBS containing 1% BSA for one hour. Then, a collected sample was inserted into each well in an amount of 100 μL, respectively, and subjected to reaction for two hours. The cells were washed three times with PBS-T, after which 50 μL of detector antibodies (anti-CCL17 antibody and anti-CCL22 antibody) were inserted into each well at 100 ng/well, and subjected to reaction for two hours. The cells were washed three times with PBS-T, after which HRP-conjugated antibodies were diluted at 1:200, then inserted thereinto in an amount of 50 μL, respectively, and then subjected to reaction for 30 minutes. The cells were fully washed with PBS-T, after which a substrate solution (TMB) was added thereto, such that absorbance thereof was measured at 450 nm.

The experiment results above were shown in FIGS. 2 and 3. As shown in FIG. 2, it was identified that there is a decrease in a level of CCL17 and CCL22 gene and protein expressions in a concentration-dependent way, as the HaCaT cells are treated with the ergostenol and the glycoside derivative thereof.

From the results above, it might be seen that the ergostenol and the glycoside derivative thereof control an inflammation-mediating expression of keratinocyte cell lines, thus exhibiting an activity of palliating dermatitis.

From the descriptions above, those skilled in the art, to which the present invention pertains, will understand that the present invention is practiced in other specific forms without changing the technical scope or essential features thereof. In this regard, it should be understood that the examples described above are illustrative in all aspects, and thus the present invention is not limited thereto. It should be understood that the scope of the present invention includes all the modifications or changed forms derived from the meaning and scope of the patent claims to be described below as well as those derived from the equivalent concepts thereto, rather than the detailed descriptions above.

The invention claimed is:

1. A compound represented by Formula 1 or pharmaceutically acceptable salts thereof:

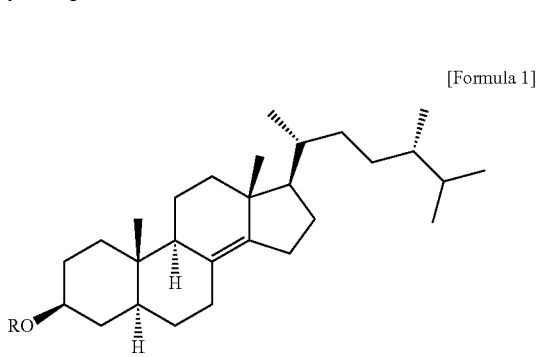

[Formula 1]

wherein R is a monosaccharide or an amino sugar.

2. The compound or pharmaceutically acceptable salts thereof of claim 1, wherein R is selected from the group consisting of

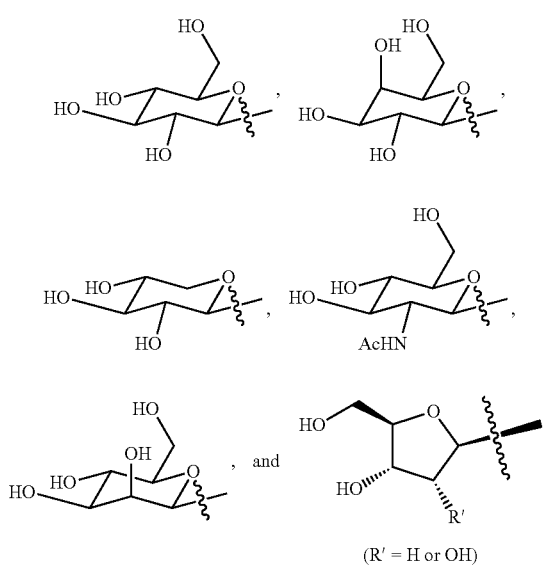

(R' = H or OH)

3. A method for treating dermatitis comprising:
administering a pharmaceutical composition comprising a compound represented by Formula 1 as an active ingredient to a subject in need thereof:

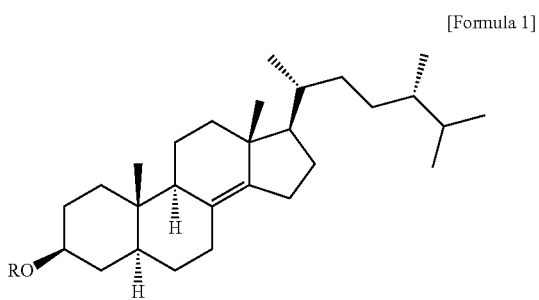

[Formula 1]

wherein R is selected from the group consisting of acetyl,

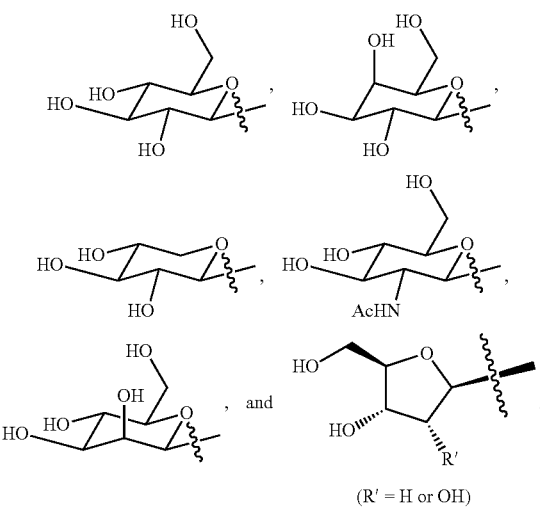

(R' = H or OH)

4. The method of claim 3, wherein the dermatitis is atopic dermatitis, contact dermatitis or seborrheic dermatitis.

5. The method of claim 4, wherein the pharmaceutical composition is a dosage form selected from the group consisting of ointments, gels, creams, patches and aerosols.

6. A method for alleviating or palliating dermatitis comprising:
administering a cosmetic composition comprising a compound represented by Formula 1 as an active ingredient to a subject in need thereof:

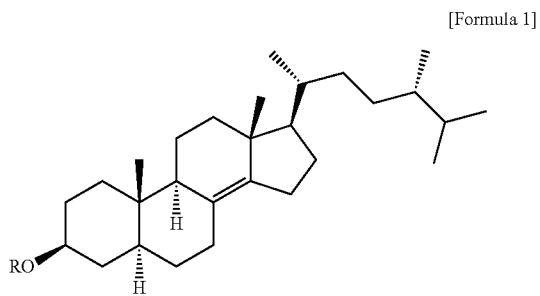

[Formula 1]

wherein R is selected from the group consisting of acetyl,

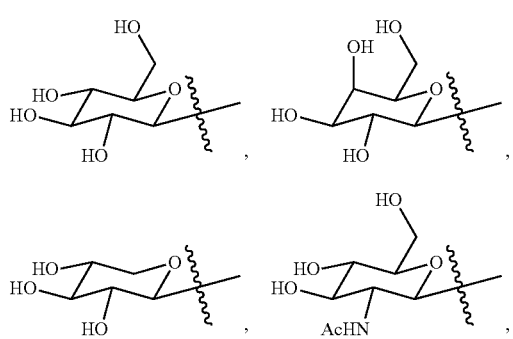

-continued

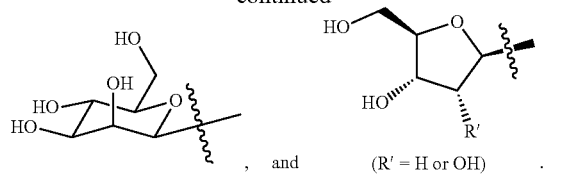

, and (R' = H or OH) 5

7. The method of claim 6, wherein the cosmetic composition is a dosage form selected from the group consisting of skin lotion, astringent lotion, nourishing lotion, nourishing cream, massage cream, essence, eye cream, eye essence, cleansing cream, cleansing foam, cleansing water, pack, powder, body lotion, body cream, body oil, body essence, makeup base, foundation, hairdye, shampoo, conditioner and body cleanser.

\* \* \* \* \*

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Forward CCL-17

<400> SEQUENCE: 1
cttctctgca gcacatcc                                                   18

<210> SEQ ID NO 2
<211> LENGTH: 19
<212> TYPE: DNA
<213> ORGANISM: Artificial Sequence
<220> FEATURE:
<223> OTHER INFORMATION: Reverse CCL-17

<400> SEQUENCE: 2
aagacctctc aaggctttg                                                  19

<210> SEQ ID NO 3
<211> LENGTH: 26
<212> TYPE: DNA
<213> ORGANISM: Artificial Sequence
<220> FEATURE:
<223> OTHER INFORMATION: Forward CCL-22

<400> SEQUENCE: 3
aggacagagc atggctcgcc tacaga                                          26

<210> SEQ ID NO 4
<211> LENGTH: 26
<212> TYPE: DNA
<213> ORGANISM: Artificial Sequence
<220> FEATURE:
<223> OTHER INFORMATION: Reverse CCL-22

<400> SEQUENCE: 4
taatggcagg gaggtagggc tcctga                                          26

<210> SEQ ID NO 5
<211> LENGTH: 22
<212> TYPE: DNA
<213> ORGANISM: Artificial Sequence
<220> FEATURE:
<223> OTHER INFORMATION: Forward b-actin

<400> SEQUENCE: 5
gcgggaaatc gtgcgtgaca tt                                              22

<210> SEQ ID NO 6
<211> LENGTH: 24
<212> TYPE: DNA
<213> ORGANISM: Artificial Sequence
<220> FEATURE:
<223> OTHER INFORMATION: Reverse b-actin

<400> SEQUENCE: 6
gatggagttg aaggtagttt cgtg                                            24